(12) United States Patent
Bonny et al.

(10) Patent No.: US 11,141,169 B2
(45) Date of Patent: Oct. 12, 2021

(54) UNIVERSAL CUT GUIDE WITH PIN ENGAGING MEMBER

(71) Applicant: Think Surgical, Inc., Fremont, CA (US)

(72) Inventors: Daniel P Bonny, Fremont, CA (US); Timothy J. Pack, Fremont, CA (US)

(73) Assignee: THINK SURGICAL, INC., Fremont, CA (US)

( * ) Notice: Subject to any disclaimer, the term of this patent is extended or adjusted under 35 U.S.C. 154(b) by 250 days.

(21) Appl. No.: 16/482,953

(22) PCT Filed: Feb. 1, 2018

(86) PCT No.: PCT/US2018/016391
§ 371 (c)(1),
(2) Date: Aug. 1, 2019

(87) PCT Pub. No.: WO2018/144699
PCT Pub. Date: Aug. 9, 2018

(65) Prior Publication Data
US 2020/0008813 A1      Jan. 9, 2020

Related U.S. Application Data

(60) Provisional application No. 62/453,876, filed on Feb. 2, 2017.

(51) Int. Cl.
*A61F 5/00* (2006.01)
*A61B 17/15* (2006.01)
*A61B 17/17* (2006.01)
*A61L 31/02* (2006.01)
*A61L 31/06* (2006.01)

(52) U.S. Cl.
CPC ............ *A61B 17/157* (2013.01); *A61B 17/17* (2013.01); *A61L 31/02* (2013.01); *A61L 31/06* (2013.01)

(58) Field of Classification Search
CPC combination set(s) only.
See application file for complete search history.

(56) References Cited

U.S. PATENT DOCUMENTS

2016/0106409 A1\* 4/2016 Moholkar ............ A61B 17/025
606/90

\* cited by examiner

*Primary Examiner* — Sameh R Boles
(74) *Attorney, Agent, or Firm* — Blue Filament Law PLLC

(57) ABSTRACT

A saw guide for guiding a surgical saw or drill includes a guide portion having one or more guide slots, the one or more guide slot or hole configured to guide a surgical saw or drill. The guide portion has an attachment portion forming a clamping slot between the guide portion and the attachment portion. A clamp locking mechanism is assembled to the guide portion and has one or more cams in contact with the attachment portion. An alignment system for surgical bone cutting procedures is provided that includes bone pins inserted within a virtual plane relative to a cut plane to be created on a subject's bone. One of the aforementioned guides is configured to be received onto the bone pins, one or more guide slots within said guide, said one or more guide slots configured to guide a surgical saw to make surgical cuts on the subject's bone.

12 Claims, 15 Drawing Sheets

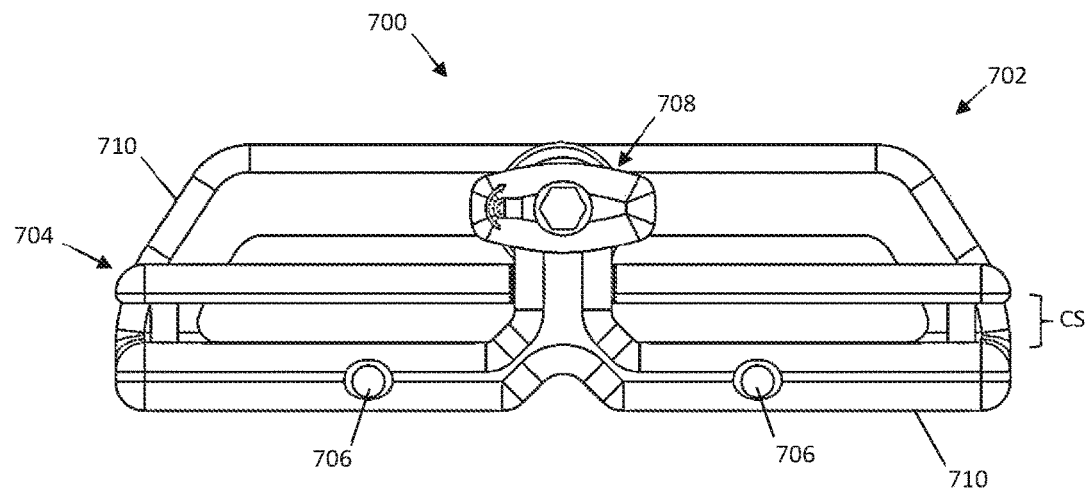
FIG. 6A
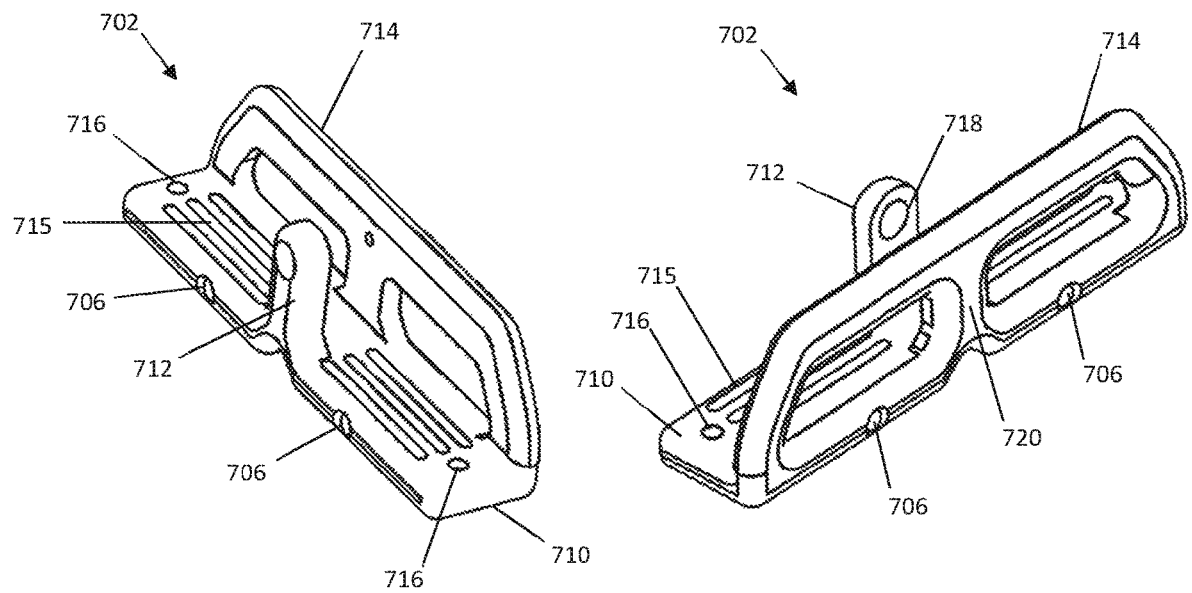
FIG. 6B
FIG. 6C

UNIVERSAL CUT GUIDE WITH PIN ENGAGING MEMBER

RELATED APPLICATIONS

This application claims priority benefit of U.S. Provisional Application Ser. No. 62/453,876 filed 2 Feb. 2017; the contents of which are hereby incorporated by reference.

FIELD OF THE INVENTION

The present invention generally relates to computer-assisted surgery, and in particular, to a plurality of guides that align on one or more pins to accurately modify a bone in orthopedic surgical applications.

BACKGROUND

Total knee arthroplasty (TKA) is a surgical procedure in which the articulating surfaces of the knee joint are replaced with prosthetic components, or implants. TKA requires the removal of worn or damaged articular cartilage and bone on the distal femur and proximal tibia. The removed cartilage and bone is then replaced with synthetic implants, typically formed of metal or plastic, to create new joint surfaces.

The position and orientation (POSE) of the removed bone, referred to as bone cuts or resected bone, determines the final placement of the implants within the joint. Generally, surgeons plan and create the bone cuts so the final placement of the implants restores the mechanical axis or kinematics of the patient's leg while preserving the balance of the surrounding knee ligaments. Even small implant alignment deviations outside of clinically acceptable ranges correlate to less than optimal outcomes and increased rates of revision surgery. In TKA, creating the bone cuts to correctly align the implants is especially difficult because the femur requires at least five planar bone cuts to receive a conventional femoral prosthesis. The planar cuts on the distal femur must be aligned in five degrees of freedom to ensure a proper orientation: anterior-posterior translation, proximal-distal translation, external-internal rotation, varus-valgus rotation, and flexion-extension rotation. Any deviation in the alignment of the planar cuts may have drastic consequences on the final result of the procedure, including patient outcomes, implant wear, and the possibility for revision surgery.

Guides, also referred to synonymously as cutting blocks, cutting jigs, alignment fixtures; are commonly used to aid in creating the bone cuts needed in orthopedic surgery. The guides include guide slots to restrict or align a bone removal device, such as an oscillating saw, in the correct bone resection plane. Guides are advantageous for several reasons. For one, the guide slots stabilize the bone removal device during cutting to ensure the bone removal device does not deflect from the desired plane due to the organic curvatures of the bone surface and as different density materials are engaged. Additionally, a single guide may contain multiple guide slots to accurately align and resect two or more cutting planes, such as a 4-in-1 cutting block. Finally, the guide slots and the working end of the oscillating saw are typically planar in shape so as to promote the creation of planar bone cuts. The advantages of using a guide are apparent, however, for the guide to confer these advantages, the guides still needs to be accurately positioned on to the bone prior to executing the cut. In fact, the placement of the guide slots on the bone remains one of the most difficult, tedious, and exacting tasks for surgeons during TKA.

Various techniques have been developed to help a surgeon correctly align the guide slots on the bone. One system and method for aligning a cutting guide on the bone is described in U.S. Provisional Patent Application No. 62/259,487 filed 24 Nov. 2015, now PCT Int'l App. No. U.S. 2016/62020 assigned to the assignee of the present application. With reference to FIG. 1A thereof, the system utilizes a computer-assisted surgical system and a patient specific surgical plan to accurately align one or more bone pins 102 onto the bone B, where a cutting guide 200 with one or more guide slots 204 is then assembled to the bone pins 102 such that the final POSE of the guide slot(s) correspond with the POSE of the desired bone cuts (FIG. 1A depicts the guide slot 204 aligned to create the planned distal cut plane CP on the femur bone B in TKA). One drawback however with the cutting guide 200 as shown in more detail in FIG. 1B, is the difficulty of assembling the cutting guide 200 onto the bone pins 102 in an efficient and time-effective manner. In general, the cutting guide 200 includes a guide portion 202 and an attachment portion 206. The guide portion 202 includes a guide slot 202 for guiding a surgical saw, and a bottom surface 208 for abutting against the bone pins 102. Currently, the attachment portion 206 assembles to the guide portion 202 via fastening elements 210 (e.g., screws) to firmly secure the cutting guide 200 to the bone pins 102. Fastening tools such as a screwdriver may be used for fastening the screws, albeit a time consuming step for the user while performing the surgery. Although, the cutting guide 200 is effective in aiding in the creation of the bone cuts, the mechanism for attaching the cutting guide 200 to the bone pins 102 can be greatly improved.

Thus, there exists a need for an improved cutting guide and method to more efficiently assemble and dissemble the cutting guide from one or more bone pins during a bone cutting procedure.

SUMMARY OF THE INVENTION

A saw guide for guiding a surgical saw to create one or more planar cuts on a bone is provided that includes a guide portion having one or more guide slots, the one or more guide slot configured to guide a surgical saw to create the one or more bone cuts on the bone. The guide portion has an attachment portion forming a clamping slot between the guide portion and the attachment portion. A clamp locking mechanism is assembled to the guide portion and has one or more cams in contact with the attachment portion so as function to adjust the size of the clamping slot as the one or more cams are rotated to lock on to a set of bone pins inserted in the bone.

A drill guide is also provided that includes a guide portion having one or more guide holes, said one or more guide holes configured to guide a surgical drill to create one or more holes in a bone. The one or more holes correspond to a location for one or more pegs on a N-in-1 cutting block. The guide portion has an attachment portion forming a clamping slot between the guide portion and the attachment portion. A clamp locking mechanism is assembled to the guide portion and has one or more cams in contact with the attachment portion so as function to adjust the size of the clamping slot as the one or more cams are rotated to lock on to a set of bone pins inserted in the bone.

An alignment system for surgical bone cutting procedures is provided that includes bone pins inserted within a virtual plane relative to a cut plane to be created on a subject's bone. One of the aforementioned guides is configured to be received onto the bone pins, one or more guide slots within said guide, said one or more guide slots configured to guide a surgical saw to make surgical cuts on the subject's bone.

BRIEF DESCRIPTION OF THE DRAWINGS

Examples illustrative of embodiments are described below with reference to figures attached hereto. In the figures, identical structures, elements or parts that appear in more than one figure are generally labeled with a same numeral in all the figures in which they appear. Dimensions of components and features shown in the figures are generally chosen for convenience and clarity of presentation and are not necessarily shown to scale. The figures are listed below.

FIG. 3A is a front view thereof, FIG. 3B is an exploded view thereof, FIG. 3C is another exploded view thereof, FIG. 3D is a side view thereof, and FIG. 3E is the improved guide clamped to bone pins;

FIG. 4A is a front view thereof, FIG. 4B is an exploded view thereof, FIG. 4C is another exploded view thereof, FIG. 4D is a side view thereof, and FIG. 4E is the second improved cutting guide clamped to bone pins;

FIG. 5A is a perspective view thereof, FIG. 5B is a side view thereof, FIG. 5C is a top view thereof, and FIG. 5D is a bottom view thereof;

FIGS. 6A-6F depicts an improved drill guide in accordance with embodiments of the invention, where FIG. 6A is a front view thereof, FIG. 6B is a rear perspective view of a guide portion of the guide, FIG. 6C is a front perspective view of the guide portion of the guide, FIG. 6D is an exploded view of the drill guide, FIG. 6E is a side view thereof, and FIG. 4F is the drill guide clamped to bone pins;

FIG. 7A is a rear perspective view thereof, FIG. 7B is a rear view thereof, FIG. 7C is a front view thereof, FIG. 7D is an exploded view of a saw guide and the insert drill guide, and FIG. 7E is an assembled view of the saw guide and insert drill guide assembled to a distal cut plane of a distal femur.

DETAILED DESCRIPTION OF THE INVENTION

Figure 1A:
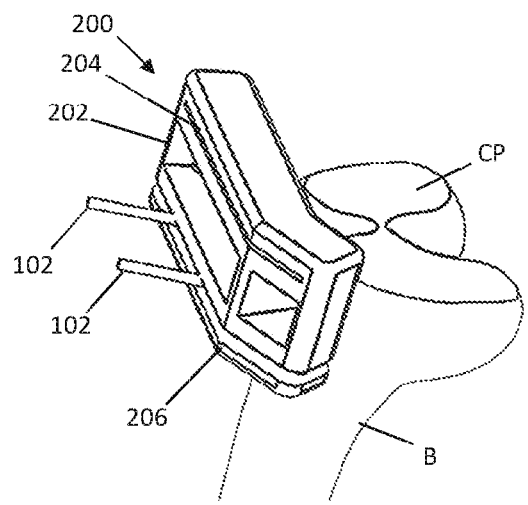
FIG. 1A depicts a prior art cutting guide clamped to bone pins with the use of fastening elements.
Figure 1B:
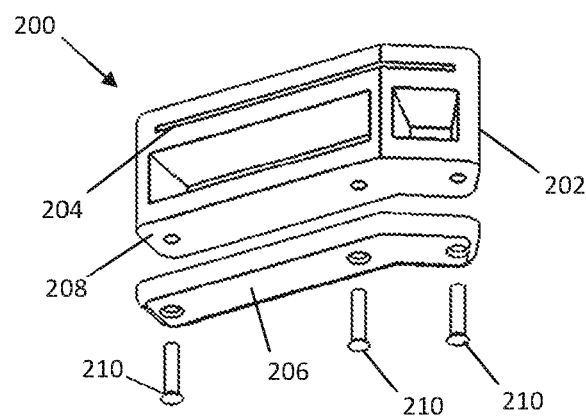
FIG. 1B depicts an exploded view of the prior art cutting guide of FIG. 1A.

The present invention has utility as a system and method to aid a surgeon in efficiently and precisely aligning a cutting guide on a patient's bone. The system and method is especially advantageous for total knee arthroplasty and revision knee arthroplasty, however, it should be appreciated that other medical applications may exploit the subject matter disclosed herein such as high tibial osteotomies, spinal reconstruction surgery, ankle arthroplasty, and other procedures requiring the precise placement of a cutting guide to aid a surgeon in creating bone cuts. In addition to usage as an adjunct to surgery, the ability to accurately attach a guide to a bone is advantageous for alignment in instances illustratively including setting a fracture, measuring growth and bone density, spine alignment, alignment of trauma plates for bone reconstruction, and aligning bone fractures using the guide as an external fixation system.

The following description of various embodiments of the invention is not intended to limit the invention to these specific embodiments, but rather to enable any person skilled in the art to make and use this invention through exemplary aspects thereof.

All publications, patent applications, patents and other references mentioned herein are incorporated by reference in their entirety.

Unless indicated otherwise, explicitly or by context, the following terms are used herein as set forth below.

As used in the description of the invention and the appended claims, the singular forms "a," "an" and "the" are intended to include the plural forms as well, unless the context clearly indicates otherwise.

Also, as used herein, "and/or" refers to and encompasses any and all possible combinations of one or more of the associated listed items, as well as the lack of combinations when interpreted in the alternative ("or").

Reference is made herein to computer-assisted surgical systems. Examples of such surgical systems illustratively include a 1-N degree of freedom hand-held surgical system, a serial-chain manipulator system, a parallel robotic system, or a master-slave robotic system, as described in U.S. Pat. Nos. 5,086,401, 6,033,415, 7,206,626, 8,876,830 and 8,961, 536, U.S. Pat. App. No. 2013/0060278, and U.S. Prov. App. No. 62/054,009. In particular embodiments, the surgical system is a 2-DOF articulating device as described in PCT App. No. U.S. 2016/62020. The surgical system may provide autonomous, semi-autonomous, or haptic control and any combinations thereof. In addition, a user may manually maneuver a tool attached to the surgical system while the system provides at least one of power, active, or haptic control to the tool.

Also, referenced herein is a surgical plan. For context, the surgical plan is created, either pre-operatively or intra-operatively, by a user using planning software. The planning software may be used to generate three-dimensional (3-D) models of the patient's bony anatomy from a computed tomography (CT), magnetic resonance imaging (MRI), x-ray, ultrasound image data set, or from a set of points collected on the bone intra-operatively. A set of 3-D computer aided design (CAD) models of the manufacturer's prosthesis are pre-loaded in the software that allows the user to place the components of a desired prosthesis to the 3-D model of the honey anatomy to designate the best fit, position, and orientation of the implant to the bone. For example, with reference to FIG. 2, a 3-D model of the patient's distal femur 302 and a 3-D model of the femoral prosthesis 304 are shown at 300. The final placement of the femoral prosthesis model 304 on the bone model 302 defines the bone cut planes (shaded regions of the bone model 302) where the bone is cut intra-operatively to receive the prosthesis as desired. In TKA, the planned cut planes on the distal femur for a conventional femoral prosthesis generally include the anterior cut plane 306, anterior chamfer cut plane 308, the distal cut plane 310, the posterior chamfer cut plane 312, the posterior cut plane 314.

The final surgical plan further includes the location of one or more virtual planes 316 defined relative to the bone. The location of the virtual plane(s) 316 is defined by the planning software using the position and orientation (POSE) of one or more planned cut planes and one or more dimensions of a guide, regardless of whether subsequently used for cutting, drilling, or alignment. A surgical system then inserts one or more bone pins 102 (shown in FIG. 1A) on the bone coincident with the virtual plane 316. A guide is then assembled to the bone pins 102 where one or more guide features (e.g., guide slots, guide holes) of the guide are in the correct POSE to accurately guide a tool to facilitate the creation of the bone cuts. Embodiments of the various inventive guides, defining of the virtual planes, and use of the bone pins are described below.

In general, embodiments of the inventive guides components disclosed herein may be made of a rigid or semi-rigid material, such as stainless steel, aluminum, titanium, polyetheretherketone (PEEK), polyphenylsulfone, acrylonitrile butadiene styrene (ABS), and the like. In a specific embodiment, the guides are made of stainless steel grade 17-4 PH for its high strength, rigidity, and resistance to corrosion, to maintain the guide's structural dimensions and making the guides suitable for continual re-use. Embodiments of the guides may be manufactured using appropriate machining tools and manufacturing/fabrication techniques known in the art.

Figure 3A:
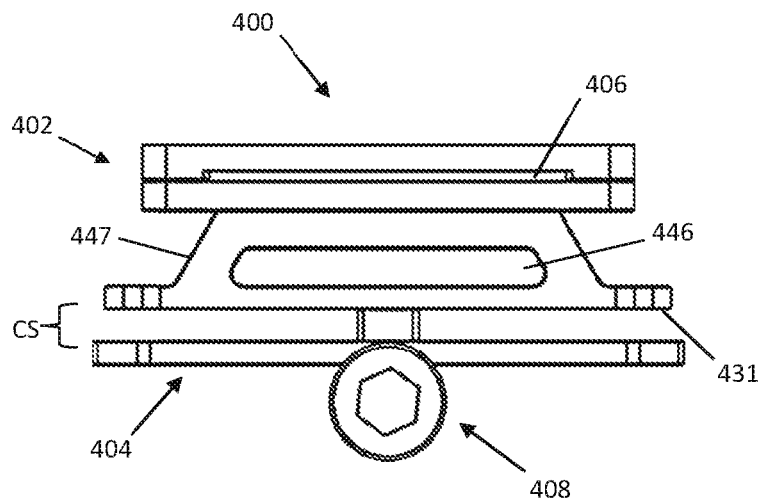
FIGS. 3A-3E depicts an improved saw guide in accordance with embodiments of the invention, where

With reference to FIGS. 3A-3D, a universal saw guide 400 to accurately aid in the creation of a planar cut is shown generally at 400. The saw guide 400 is configured to clamp to a plurality of pins inserted on the bone and guide a surgical saw to create the planned planar cut. FIG. 3A depicts a front view of the saw guide 400 where the saw guide 400 generally includes a guide portion 402, an attachment portion 404, and a clamp locking mechanism 408. The guide portion 402 includes a guide slot 406 for guiding a surgical saw in creating a planned planar cut (e.g., the distal planar cut 310 on the femur bone B), and a bottom surface 431 that abuts against one or more bone pins 102 located on the bone B. The attachment portion 404 is assembled to the guide portion 402 to form a clamping slot CS to clamp onto the bone pins 102 with the clamp locking mechanism 408.

Figure 3B:
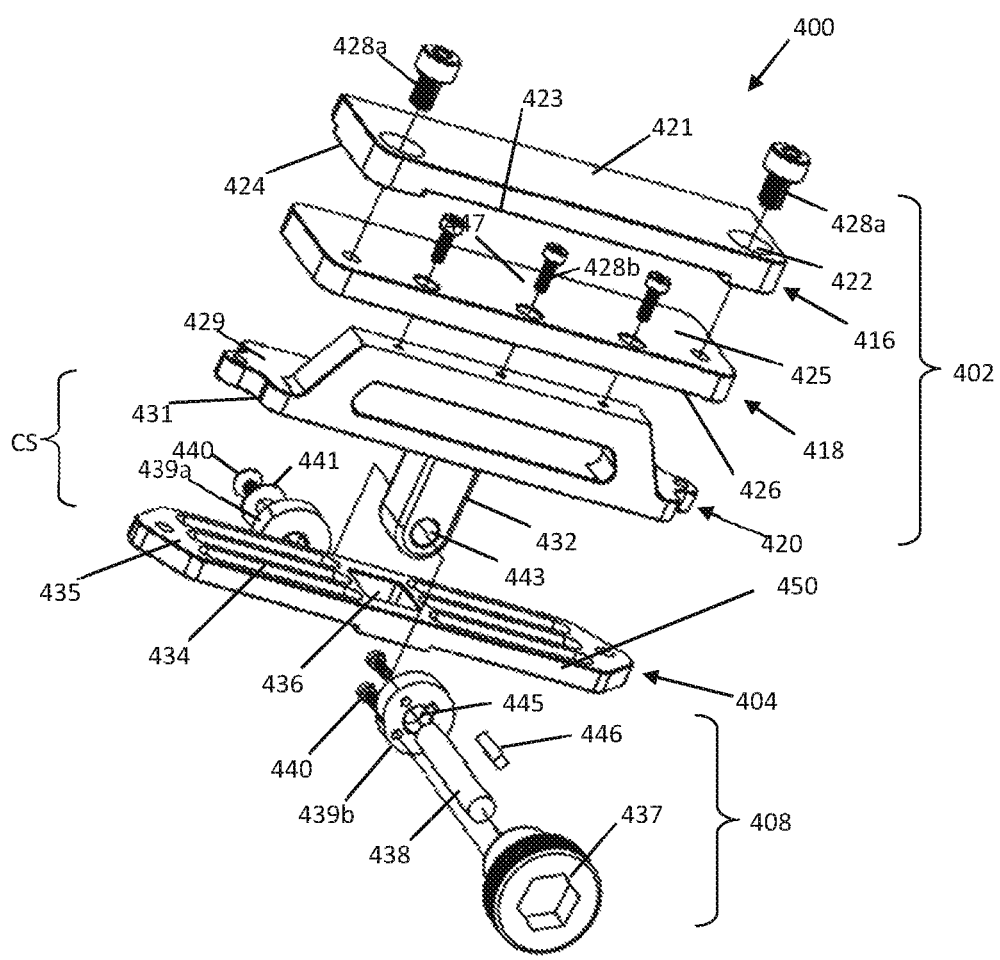

With reference to FIG. 3B, the saw guide 400 is shown in an exploded view. In a specific embodiment, the guide portion 402 includes a first plate 416, a second plate 418, and a stationary jaw plate 420. The first plate 416 includes a top surface 421 and a bottom surface 424, where a portion of the bottom surface 424 is indented to form an indentation 423. The second plate 418 includes a top surface 425, a bottom surface 426, and assembles to the first plate 416 via fastening elements (e.g., screws) 428a. When the first plate 416 is assembled to the second plate 418, the indentation 423 of the first plate 416 forms the guide slot 406.

The stationary jaw plate 420 holds one side of the bone pins 102 and is also configured to facilitate the assembly of: the guide portion 402; the attachment portion 404; and the clamp locking mechanism 408. In specific embodiments, the stationary jaw plate 420 includes a top surface 429, and a bottom surface 431 having a plurality of grooves. A projection 447 extends from at least a portion of the top surface 429 of the jaw plate 420 to increase the distance between the clamping slot CS and the guide slot 406. The projection 447 also increases the span of which the saw guide 400 contacts the bone B to increase the stability of the saw guide 400 on the bone B as the user creates a planar cut. The first plate 416 and second plate 418 may assemble to a top portion of the projection 447 via fastening elements 428b. The projection 447 may further include a drill guide slot 446 extending through a portion of the projection 447. The drill guide slot 446 is configured to receive an insert drill guide 750 as further described below with reference to FIGS. 7A-7E. The drill guide slot 446 further reduces the overall weight of the saw guide 400 for easier handling. In other embodiments, there is no projection 447 where the first plate 416 and second plate 418 assemble directly to the top surface 429 of the stationary jaw plate 420.

The saw guide 400 further includes at least one coupling rod 432 extending from the bottom surface 431 of the stationary jaw plate 420. The coupling rod 432 is adapted to receive the attachment portion 404 to form the clamping slot CS, and facilitate the assembly of the clamp locking mechanism 408 to the saw guide 400.

In a particular inventive embodiment, the attachment portion 404 is a moveable jaw plate 450. The movable jaw plate 450 has a top surface 435 with a plurality of grooves 434, and an opening 436 adapted to receive the coupling rod 432 of the stationary jaw plate 420. The grooves on the surfaces (431, 435) of the jaw plates (404, 420) increase the clamping pressure and mechanical friction between the bone pins 102 and the saw guide 400 to hold the guide 400 tightly in place. The grooves essentially decrease the contact surface area between the bone pins 102 and the saw guide 400, which increases the clamping pressure even when the same clamping force is applied. Friction force is dependent on pressure, so decreasing the surface area increases friction which means the saw guide 400 is less able to move on the bone pins 102 with the same clamping force.

Figure 3C:
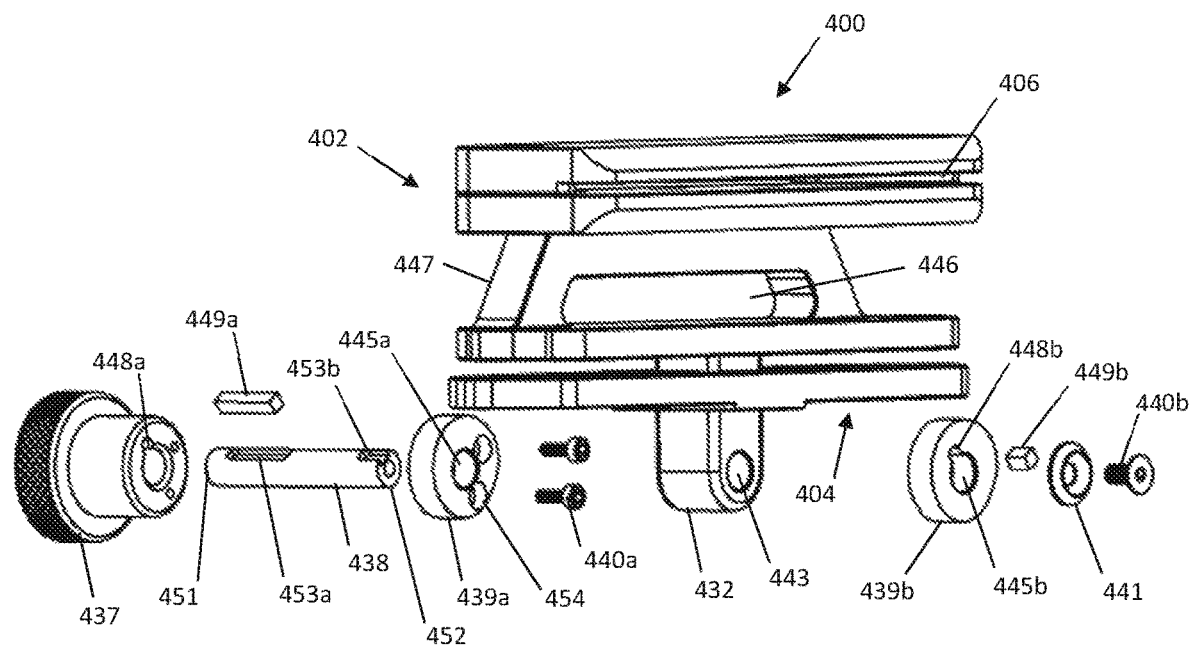

The clamp locking mechanism 408 is configured to allow a user to adjust the tightness and size of the CS (i.e., the position of the attachment portion 404 relative to the guide portion 402). The clamp locking mechanism 408 allows the user to quickly and efficiently removably secure the saw guide 400 to the bone pins 102. In a particular inventive embodiment, with reference to FIGS. 3B and 3C, the clamp locking mechanism 408 includes a rotating knob 437, an assembly shaft 438 having a one or more keyseats (453a, 453b), one or more cams (439a, 439B) having cam holes (445a, 445b), one or more keyways (448a, 448b), one or more washers 441, one or more keys (449a, 449b), and a plurality of screws 440. The assembly of the clamp locking mechanism 408 will now be described in more detail. With reference to FIG. 3C, the assembly shaft 438 passes through the opening 443 of the coupling rod 432, and holds a first cam 439a on one side of the coupling rod 432 and a second cam 439b on an opposing side of the coupling rod 432. With cams on opposing sides of the coupling rod 432, a uniform pressure is applied to the attachment portion 404 as the user rotates the rotating knob 437. A first set of fastening elements 440a insert into a set of counterbores 454 located on the first cam 439a, and fasten into a set of screw holes located on the rotating knob 437. This assembles the first cam 439a with the rotating knob 437. The assembly shaft 438 further includes a first end 451 and a second end 452, where the first end 451 fits into a portion of the rotating knob 437, and the second end 452 includes a screw hole to receive a screw 440b. The screw 440b and a washer 441 screw into the second end 452 of the assembly shaft 438 to complete the assembly of the clamp locking mechanism 408. In addition, one or more keys (449a, 449b) are used to increase rotational torque and prevent rotation between the shaft 438 and the cams (439a, 439b) as the user rotates the rotating knob 437. In particular, a first key 449a lies within a first keyseat 453a located on the assembly shaft 438 and fits into: i. a first keyway 448a associated with the knob 437; and ii. a second keyway (not shown) associated with the first cam 439a. A second key 449b lies within a second keyseat 453b located on the assembly shaft 438 and fits into a second keyway 448b associated with the second cam 439b.

It should be appreciated that the cams described herein may be eccentric cams, egg-shaped cams, ellipse cams, hexagon cams, dual cams, and combinations thereof. As the user rotates the rotating knob 437, the cams rotate causing the attachment portion 404 to translate either towards or away from the bone pins 102. Therefore, a user can quickly assemble the guide 400 to the bone pins 102 by rotating the rotating knob 437. In specific inventive embodiments, the cams are dimensioned to cause the attachment portion 404 to translate a specific distance to firmly tighten and release the saw guide 400 to and from the bone pins 102. The cam dimensions may be a function of the width of the bone pins 102 and how tight the guide 400 needs to assemble to the bone pins 102 while still allowing the saw guide 400 to be released from the bone pins 102. The design of the cam(s) to tighten the clamping slot CS a specific distance to clamp onto a specific structure (i.e., the bone pins) deviates from a typical type of adjustable clamp such as a traditional vice or a C-clamp, which are designed to clamp onto structures having various dimensions. In a particular inventive embodiment, the cam(s) is designed to prevent over-tightening. The clamping distance (i.e., how much the attachment portion 404 translates relative to the guide portion 402) is determined by the change in diameter of the cam(s), where the change in diameter is designed to be intentionally slight such that the user cannot overtighten the saw guide 400 to the bone pins 102. In a specific embodiment, the change in diameter is between 2 mm and 4 mm. In other inventive embodiments the change in diameter is less than 2 mm.

In a particular inventive embodiment, the saw guide 400 includes one or more springs (not shown) positioned between the guide portion 402 and the attachment portion 404. The springs are configured to keep the clamping slot CS expanded when the cams (439a, 439b) are loosened. Therefore, the attachment portion 404 remains fully expanded from the guide portion 402 unless the cam is turned. This also prevents the attachment portion 404 from unintentionally engaging and/or mating with the guide portion 402 as the user tries to assemble the saw guide 400 to the bone pins 102.

In a specific inventive embodiment, the saw guide 400 includes a mechanical stop, such as one or more set screws positioned between the attachment portion 404 and the cam locking mechanism 408. The mechanical stop sets the maximum expansion distance of the clamping slot CS so that the cams (439a, 439b) are unloaded when fully loosened. Without a mechanical stop to limit the expansion of the clamping slot CS, the attachment portion 404 can impose loads to the cam locking mechanism 408 even when the cams (439a, 439b) are fully loosened. This loading can cause major issues with wear and binding. Therefore, the mechanical stop arrests the attachment portion 404 before making contact with locking mechanism 408 as the cams (439a, 439b) are loosened. In other words, the cams (439a, 439b) lose contact with the attachment portion 404 when the cams (439a, 439b) are in a fully loosened position and are therefore not loaded.

Figure 3D:
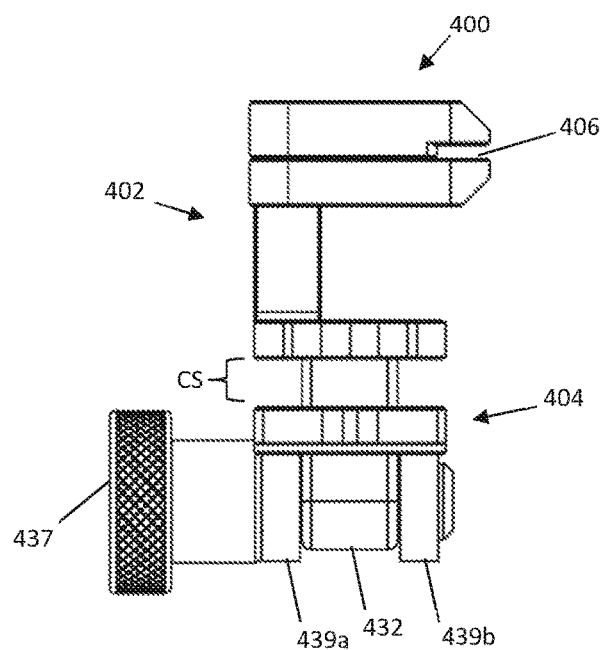
Figure 3E:
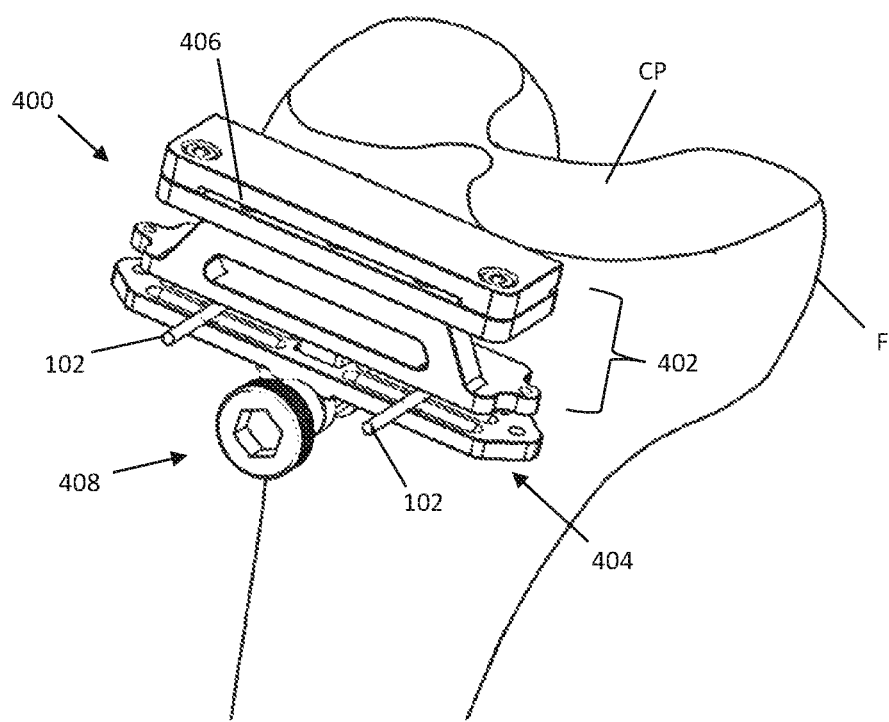

FIG. 3D depicts a side view of the assembled saw guide 400 and FIG. 3E depicts the saw guide 400 clamped to the bone pins 102 on the femur F.

Figure 4A:
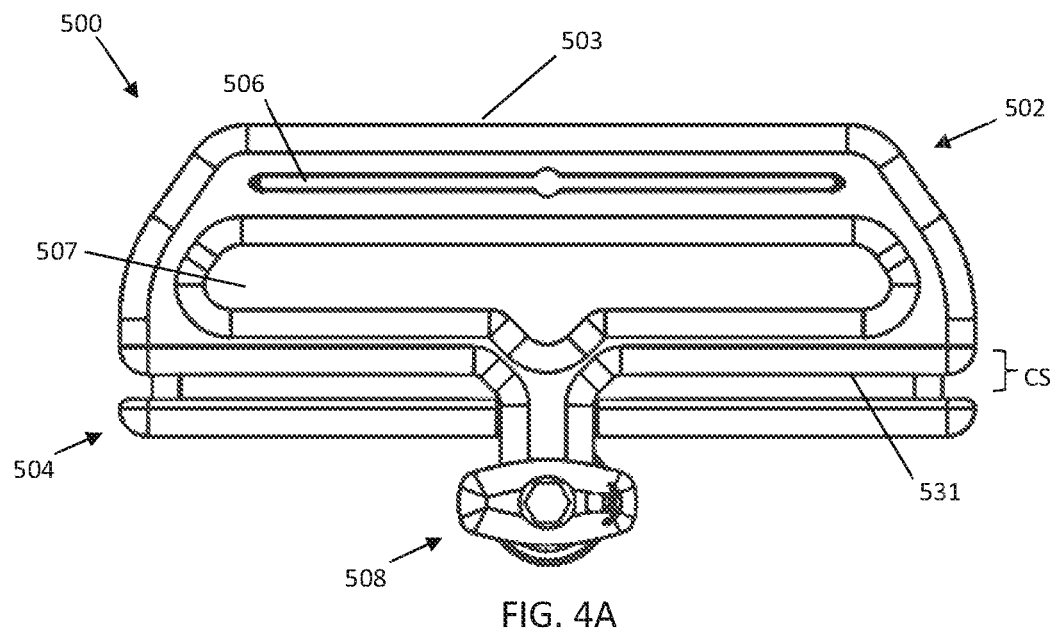
FIGS. 4A-4E depicts a second improved saw guide in accordance with embodiments of the invention, where
Figure 4B:
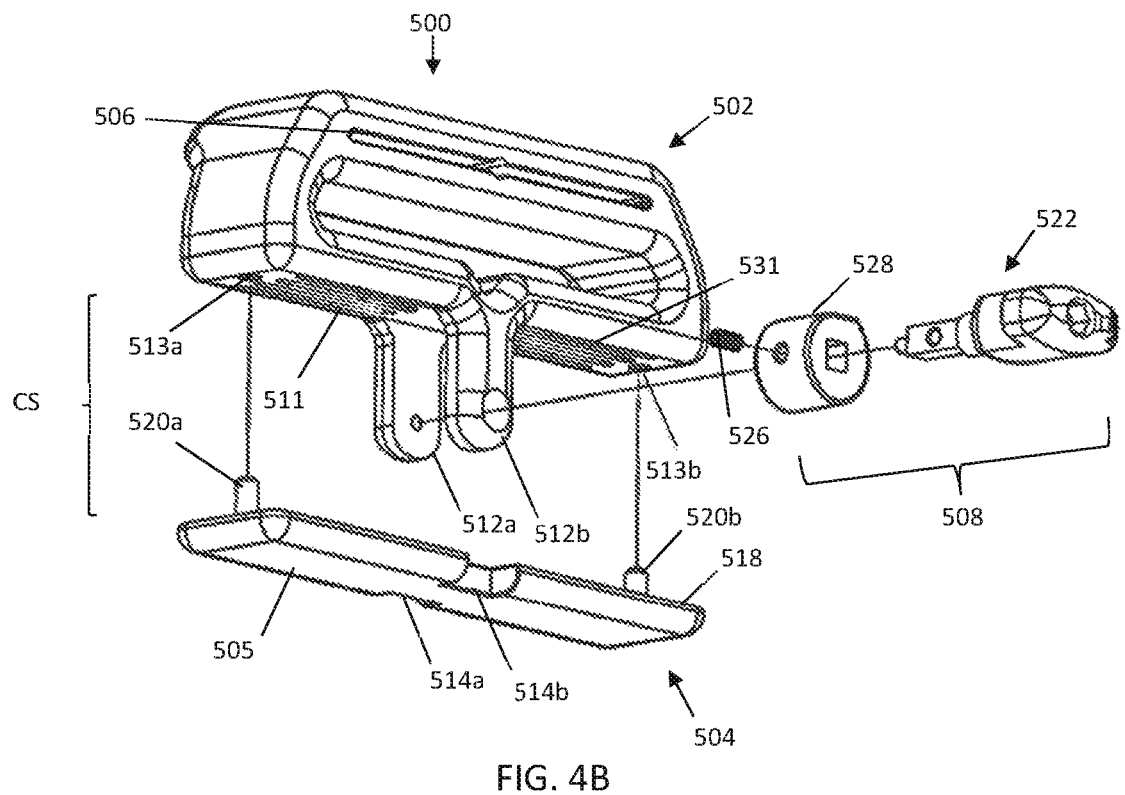
Figure 4C:
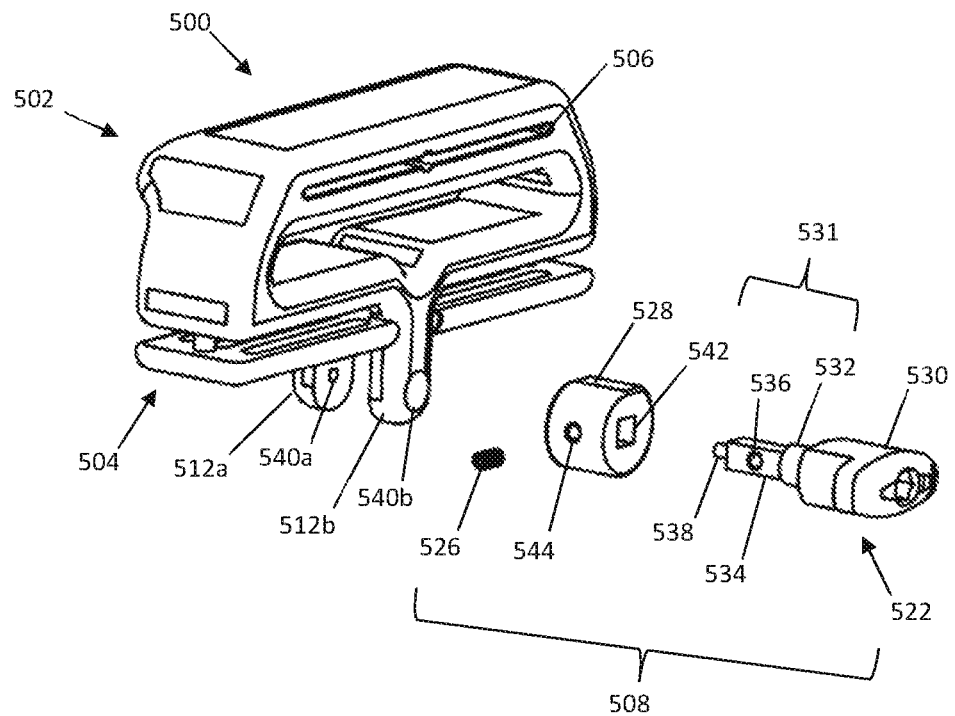

With reference to FIGS. 4A to 4D, another inventive embodiment and design of a saw guide 500 is shown. FIG. 4A depicts a front view of the assembled saw guide 500 and FIG. 4B depicts the saw guide 500 in an exploded view. The saw guide 500 generally includes a guide portion 502, an attachment portion 504 and a clamp locking mechanism 508. The guide portion 502 and the attachment portion 504 are assembled to form a clamping slot CS therebetween to clamp the bone pins 102 to the guide 500 with the aid of the clamp locking mechanism 508.

In a specific inventive embodiment, the guide portion 502 is a stationary jaw body 503. The stationary jaw body 503 includes a guide slot 506 extending through the body 503 for guiding a surgical saw in creating planar cuts, a bottom surface 531 having a plurality of grooves that contact the bone pins 102, and at least two coupling rods (512a, 512b) extending from a first edge and an opposing edge of the bottom surface 531 to facilitate the assembly of the guide portion 502, attachment portion 504, and clamp locking mechanism 508. The guide portion 502 may further include a drill guide slot 507 extending through the stationary jaw body 503 parallel to and offset from the guide slot 506. The drill guide slot 507 receives an insert drill guide 750 as further described below with reference to FIGS. 7A-7E. The drill guide slot 507 further reduces the overall weight of the saw guide 500 for easier handling.

In a particular inventive embodiment, the attachment portion 504 is a movable jaw plate 505. The moveable jaw plate 505 includes a top surface 518 having a plurality of grooves for contacting the bone pins 102, one or more notches (514a, 514b) notched into one or more edges of the plate 505, and at least two pins (520a, 520b) projecting from opposing sides of the top surface 518. The notches (514a, 514b) receive the coupling rods (512a, 512b) of the guide portion 502 to facilitate the assembly of the guide 500 and to form the clamping slot CS between the guide portion 502 and attachment portion 504. The at least two guide pins (520a, 520b) fit within at least two holes (513a, 513b) located on the bottom surface 531 of the guide portion 502. The guide pins (520a, 520b) are designed and dimensioned to prevent the clamping slot CS from closing beyond a distance that is slightly smaller than the diameter of the bone pins 102. The plurality of grooves on the top surface 518 of the attachment portion 504 and the plurality of grooves 511 on the bottom surface 531 of the guide portion 502 increase the clamping pressure and mechanical friction between the bone pins 102 and the guide 500 as described above.

The clamp locking mechanism 508 is configured to allow a user to adjust the tightness and size of the CS (i.e., the position of the attachment portion 504 relative to the guide portion 502). The clamp locking mechanism 508 allows the user to quickly and efficiently removably secure the guide 500 to the bone pins 102. In a specific inventive embodiment, with reference to FIG. 4C, the clamp locking mechanism 508 generally includes a rotating knob 522, at least one cam 528, and a set screw 526. More specifically, the rotating knob 522 includes a handle 530 to permit a user to rotate the cam 528, and a connector piece 531 to assemble the cam 528 to the guide 500. The connector piece 531 includes a first shaft 532 extending away from the handle 530, a rectangular peg 534 having a set screw hole 536 projecting away from the first shaft 532, and a second shaft 538 extending away from the rectangular peg 534. The cam 528 includes a rectangular hole 542 and a set screw hole 544.

When assembled, the second shaft 538 pivotally sits into a corresponding hole 540a associated with a first coupling rod 512a of the guide portion 502, and the first shaft 532 pivotally sits into a corresponding hole 540b associated with a second coupling rod 512b of the guide portion 502. The cam 528 fits between the first coupling rod 512a and the second coupling rod 512b. The rectangular peg 534 of the knob 522 is connected with the rectangular hole 542 of the cam 528 and ensures the cam rotates as the user rotates the knob 522. The cam 528 is securely fixed to the knob 522 using the set screw 526 screwed through the set screw holes (536, 544), which additionally secures the locking mechanism 508 to the guide 500. In a particular inventive embodiment, the diameter of the second shaft 538 is less than a cross-section of the rectangular peg 534 and the diameter of the first shaft 532 to facilitate assembly.

Figure 4D:
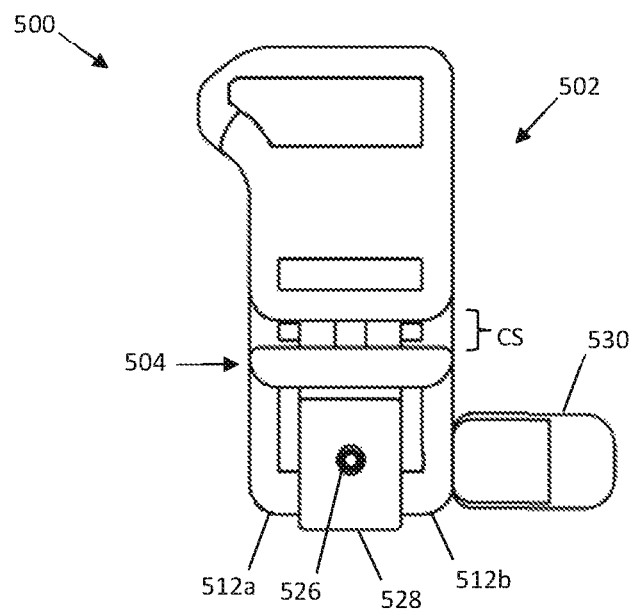
Figure 4E:
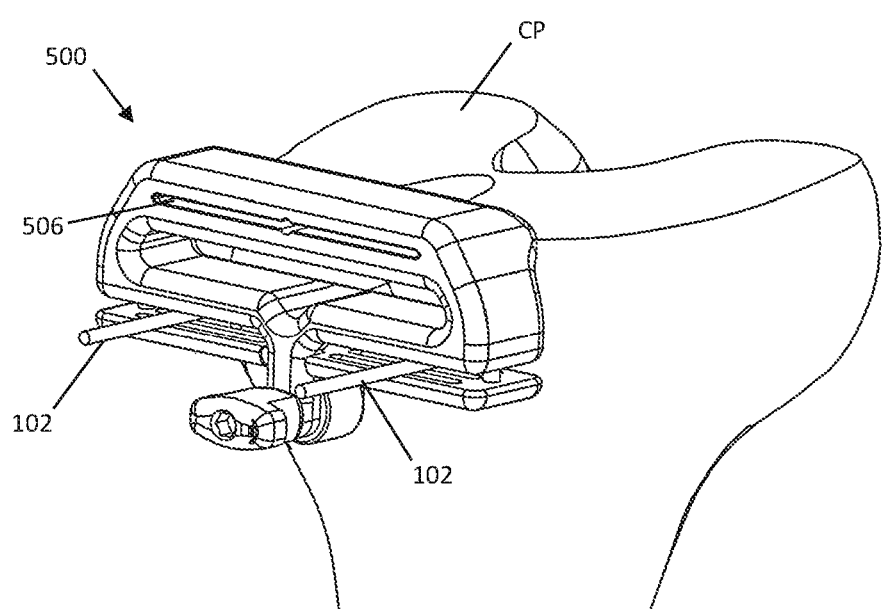

FIG. 4D depicts a side view of the assembled guide 500 and FIG. 4E depicts the guide 500 clamped to the bone pins 102 on the femur F.

In a particular inventive embodiment, the spring and mechanical stop as described for the guide 400 shown in FIGS. 3A-3E may be included in the design of the guide 500. However, in a specific inventive embodiment, the guide 500 does not require a spring or a mechanical stop, where the guide 500 is designed such that the maximum clamping distance is limited by contact with the cam, and the two guide pins (520a, 520b) prevent closure of the clamping slot CS beyond a distance that is slightly smaller (e.g., 0.5 mm to 2 mm) than the diameter of the bone pins 102.

The guide 500 shown in FIGS. 4A-4E has several advantageous design aspects compared to the guide 400 shown in FIGS. 3A-3E. First, the guide portion 502 of guide 500 is a monolithic structure requiring no additional assembly or sub-components as opposed to the guide portion 402 of guide 400. Second, the cam locking mechanism 508 requires fewer components to assemble, where only one cam 528 may be used to efficiently clamp the guide 500 to the bone pins 102. The fewer components of the guide 500 also means the overall weight is less and the components of the guide 500 are more easily replaced when worn or damaged. For example, the attachment portion 504 and/or the guide portion 502 may turn freely beyond the largest diameter of the cam 528 as the attachment portion 504 and/or guide portion 502 become worn, they will make the need to replace them obvious. Likewise, the cam 528 may need to be replaced as it wears. Therefore, the components of guide 500 are more accessibly replaced compared to guide 400.

Figure 5A:
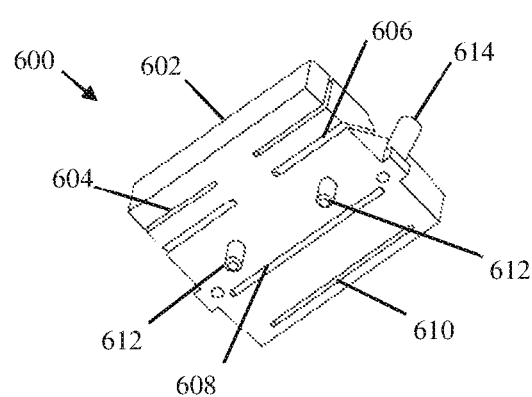
FIG. 5A-5D depict a prior art 4-in-1 cutting block, where
Figure 5B:
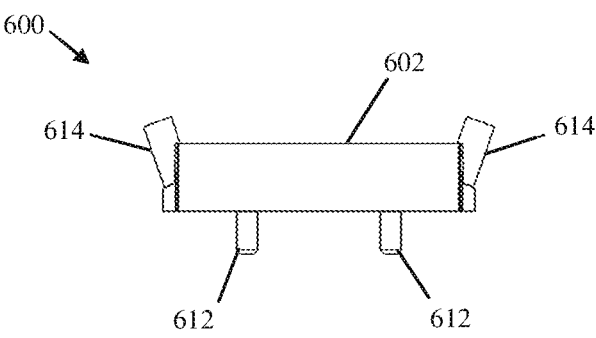
Figure 5C:
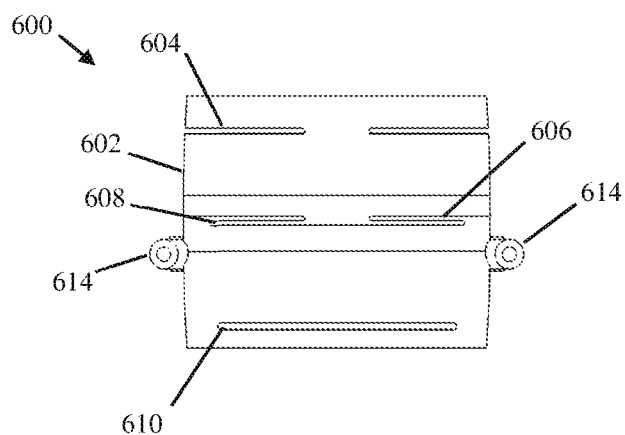
Figure 5D:
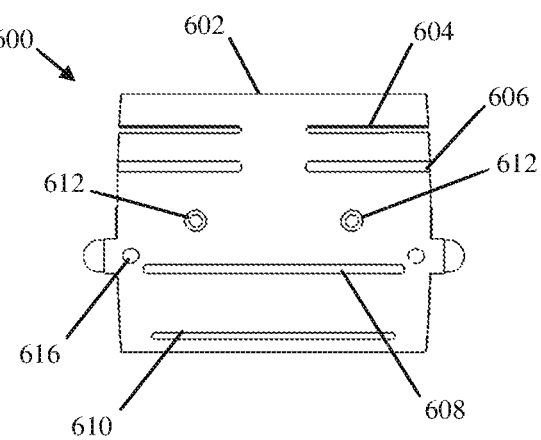

With respect to FIGS. 5A-5D, a prior art 4-in-1 cutting block 600 is shown. The 4-in-1 cutting block 600 aids in the creation of several bone cut planes in TKA. FIG. 5A is a perspective view of the 4-in-1 cutting block, FIG. 5B is a side elevation view thereof, FIG. 5C is a top plan view thereof, and FIG. 5D is a bottom plan view thereof. The 4-in-1 cutting block 600 may be made of materials similar to that of the guide (400, 500). The 4-in-1 cutting block 600 is manufactured to include a body 602 with several guide slots. In particular, the 4-in-1 cutting block 600 includes a posterior guide slot 604, a posterior chamfer guide slot 606, an anterior chamfer guide slot 608, and an anterior guide slot 610. The cutting block 600 also includes two or more pegs 612 that fit into holes drilled on the distal cut plane 310, and two pin securing guides 614 to receive pins to secure the cutting block 600 on the distal cut plane CP on the femur F. Although a 4-in-1 cutting block 600 is described herein, it should be appreciated that any N-in-1 cutting block for creating additional cut-planes on the bone may be aligned and assembled on the bone using the embodiments described herein. An N-in-1 cutting block can account for femoral prostheses having greater than 5 planar contact surfaces (for reference and clarity, the femoral prosthesis 304 shown in FIG. 2 has 5 planar contact surfaces including the posterior contact surface 318 that mates with the posterior cut plane 314).

An N-in-1 block is useful for quickly creating several cut planes on the bone B. However, the cutting block still needs to be accurately assembled on the bone B in the correct POSE to accurately create the cut planes as planned A method for creating the holes for the pegs 612 of the cutting block 600 to accurately assemble the cutting block 600 to the bone B is described in U.S. Provisional Patent Application No. 62/259,487 filed 24 Nov. 2015. Briefly, the method similarly uses a plurality of bone pins 102 inserted on a virtual pin plane. A guide is fastened to the bone pins 102 to aid in the creation of holes that receive the pegs 612 of the cutting block 600 such that the cutting block 600 is aligned in the planned POSE. However, the guide still requires fastening elements to tighten the guide to the bone pins 102. An improved guide to overcome this problem is described below.

Figure 6D:
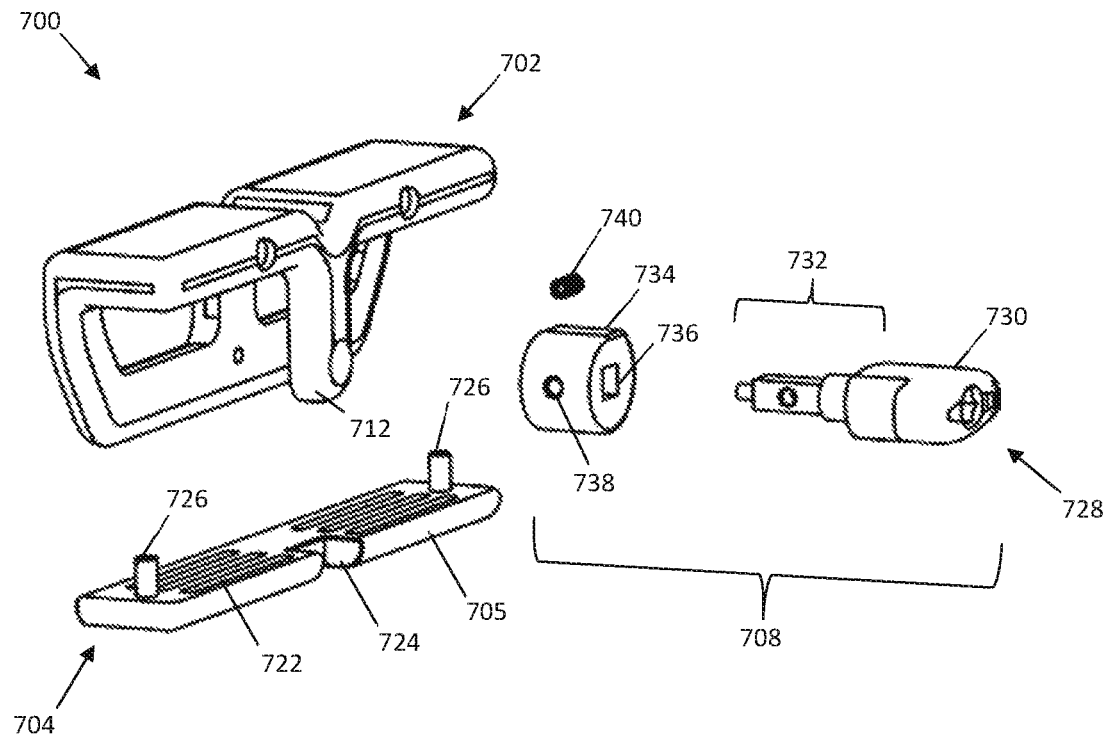

In a specific inventive embodiment, FIGS. 6A-6F depict a drill guide 700 for creating the holes on the distal cut plane CP to receive the cutting block pegs 612 of the cutting block 600 in the planned POSE on the bone. FIG. 6A depicts a rear view of the drill guide 700 fully assembled. In general, the drill guide 700 includes a guide portion 702 having guide holes 706 for guiding a surgical drill to create the holes for the pegs 612, an attachment portion 704 to form a clamping slot CS between the guide portion 702 and attachment portion 704, and a clamp locking mechanism 708 to adjust the clamping distance of the clamping slot CS to permit a user to removably secure the drill guide 700 to the bone pins 102.

With reference to FIGS. 6B-6C the guide portion 702 is shown in more detail in a rear perspective view and a front perspective view, respectively. In a specific inventive embodiment, the guide portion 702 includes a stationary jaw plate 710 having a clamping surface 715 with a plurality of grooves for contacting the bone pins 102, a coupling rod 712 extending from one side of the clamping surface 715 to facilitate the assembly of the drill guide 700, and a projection 714 extending from an opposing side of the clamping surface 715 to further facilitate the assembly of the drill guide 700 as well as providing a structure to contact a portion of the bone B for stability. The stationary jaw plate 710 further includes the two or more guide holes 706 and two or more pin holes 716. The two or more guide holes 706 are bored through the jaw plate 710 on a lateral side of the plate 710 with respect to the clamping surface 715, where the guide holes 706 are spaced a distance apart corresponding to the distance between two or more pegs 612 associated with an N-in-1 cutting block 600. The two or more pin holes 716 receive two or more guide pins 726 (shown in FIG. 6D) associated with the attachment portion 704. The coupling rod 712 is received in a notch 724 associated with the attachment portion 704 (shown in FIG. 6D) and further includes an opening 718 for receiving and holding a shaft associated with the clamp locking mechanism 708. The projection 714 includes a bone contacting surface 720 that makes direct contact with the distal cut plane CP on the femur F. The projection 714 is designed to increase the contact surface area between the drill guide 700 and the distal cut plane CP to increase stability. Accordingly, the contacting surface 720 is flat to mate with the planar distal cut plane CP.

Figure 6E:
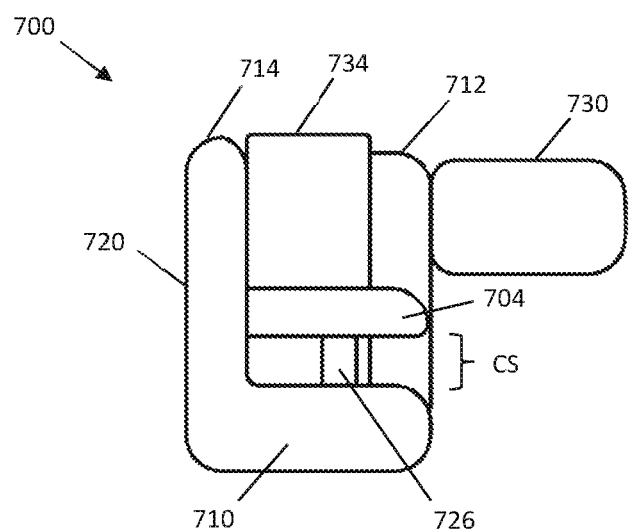
Figure 6F:
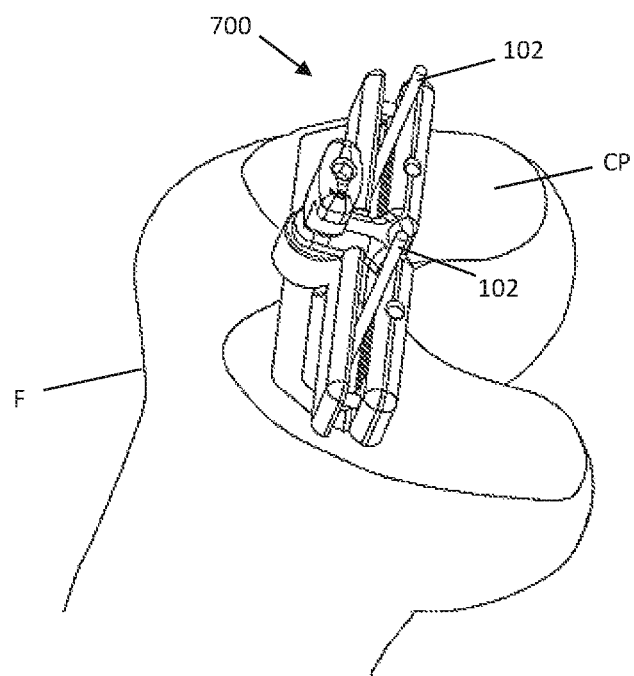

With reference to FIG. 6D, the drill guide 700 is shown in an exploded view. In a particular inventive embodiment, the attachment portion 704 is a moveable jaw plate 705. The movable jaw plate 705 includes a clamping surface 722 having a plurality of grooves, the notch 724 for receiving the coupling rod 712, and two or more guide pins 726 that fit in the pin holes 716 of the guide portion 702. The clamping slot CS is formed between the clamping surfaces (715, 722) of the guide portion 702 and attachment portion 704. The guide pins 726 have the same function as the aforementioned guide pins 520 associated with the attachment portion 504 of the guide 500 shown in FIGS. 4A-4E. The clamp locking mechanism 708 has the same design as the aforementioned clamp locking mechanism 508 associated with the guide 500 shown in FIGS. 4A-4E. Briefly, the clamp locking mechanism 508 generally includes a rotating knob 728, at least one cam 734 and a set screw 740. The rotating knob 728 includes a handle 730, and a connector piece 732 having the same design of connector piece 531. The cam 734 includes a rectangular opening 736 and a set screw hole 738, where a set screw 740 secures the cam 734 and knob 728 to the drill guide 700. Therefore, a user may rotate the rotating knob 728 to adjust the size of the clamping slot CS to efficiently secure and remove the drill guide 700 from the bone pins 102. FIG. 6E depicts a side view of the fully assembled drill guide 700 and FIG. 6F illustrates the drill guide 700 clamped on the bone pins 102 with the bone contacting surface 720 mated with the distal cut plane CP.

In a specific inventive embodiment, the stationary jaw plate 710 of the drill guide 700 includes two or more pairs of guide holes to accommodate for different sizes of N-in-1 cutting blocks. Each pair of guide holes is distanced apart corresponding to the distance between the pegs 612 for differently sized cutting blocks. For example, a first N-in-1 cutting block has pegs 612 distanced 20 mm apart, and a second N-in-1 cutting block has pegs distanced 25 mm apart. The stationary jaw plate 710 then includes a first pair of guide holes spaced 20 mm apart, and a second pair of guide holes spaced 25 mm apart. Therefore, the drill guide 700 may be used for different sized patients, which can greatly reduce manufacturing costs.

Figure 7A:
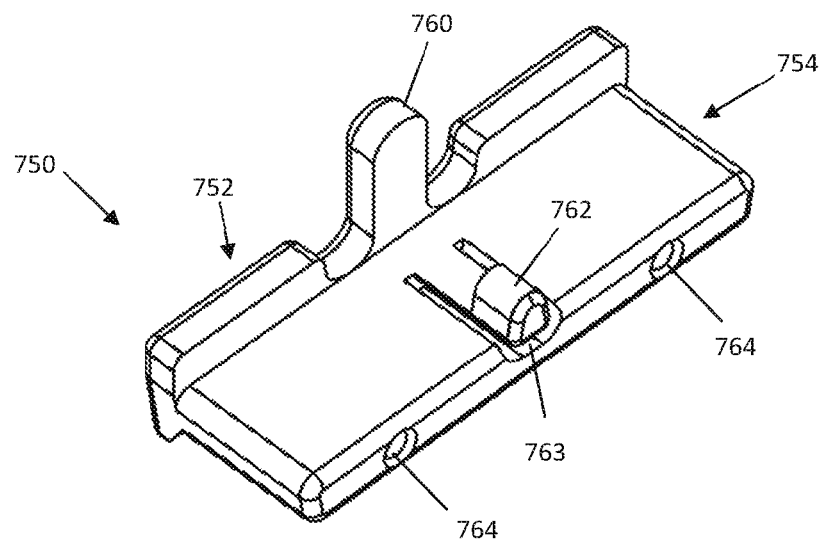
FIGS. 7A-7E depict an insert drill guide in accordance with embodiments of the invention, where
Figure 7B:
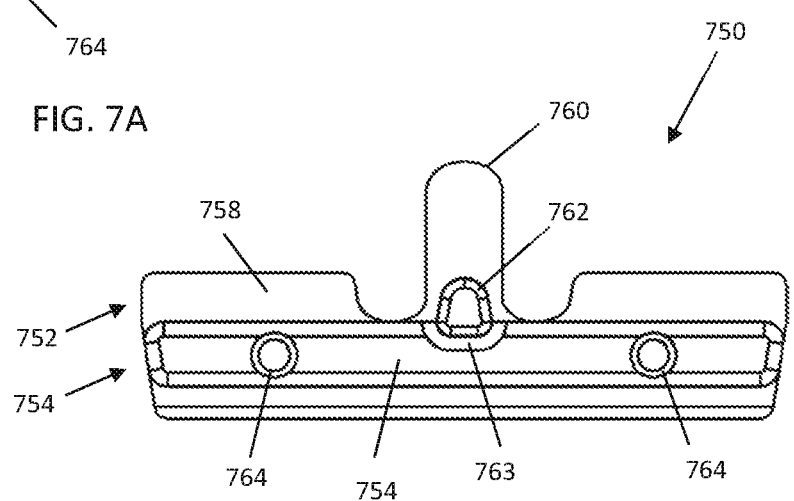
Figure 7C:
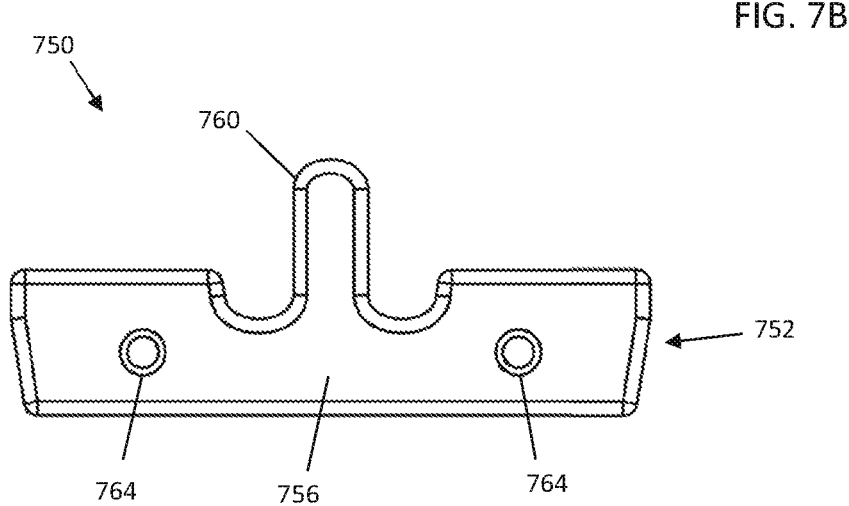

With reference to FIGS. 7A-7C, an insert drill guide 750 is shown. The insert drill guide 750 is configured to assemble to a saw guide (400, 500) for guiding a surgical drill to create the holes on the distal cut plane CP to receive pegs 612 of an N-in-1 cutting block 600 in the planned POSE. FIG. 7A is front view of insert drill guide 750, FIG. 7B is a rear view thereof, and FIG. 7C is a rear perspective view thereof. In specific embodiments, the insert drill guide 750 includes a stopper portion 752 and an insert portion 754. The stopper portion 752 is configured to abut against a face of a saw guide (400, 500). The stopper portion 752 is an elongated body having a front face 756 and a back face 758. A center region 760 of the stopper portion 752 between the front face 756 and the back face 758 projects outwards to increase the surface area of the front face 756 and back face 758 at the center region 760. The insert portion 754 is configured to be inserted in a drill guide slot (446, 507) of a saw guide (400, 500). The insert portion 754 is an elongated body located at a right angle from the stopper portion 752, such that the stopper portion 752 and insert portion 754 are roughly in the form of the letter 'T'. The insert portion 754 may further include a built-in spring 762 positioned at the center of and end of the insert portion 754 and perpendicular to the back face 758 of the stopper portion 752. The built-in spring 762 may be in the form of a cantilever created by removing a segment of material 763 in the insert portion 754 below the desired position for the cantilever. A bulb at the end of the cantilever protrudes above the insert portion 754 to compress against a side wall of a drill guide slot (446, 507) of a saw guide (400, 500) to hold the insert drill guide 750 in a saw guide (400, 500) when assembled as further described below. The insert drill guide 750 further includes at least one pair of holes 764 drilled through the stopper portion 752 and the insert portion 754. The holes 764 being drilled perpendicular to the front face 756 and back face 758 of the stopper portion 752. The holes 764 being spaced a distance apart corresponding to the distance between the pegs 612 of an N-in-1 cutting block 600. In a specific embodiment, the holes 764 are symmetrical about a center axis of the insert drill guide 750.

Figure 7D:
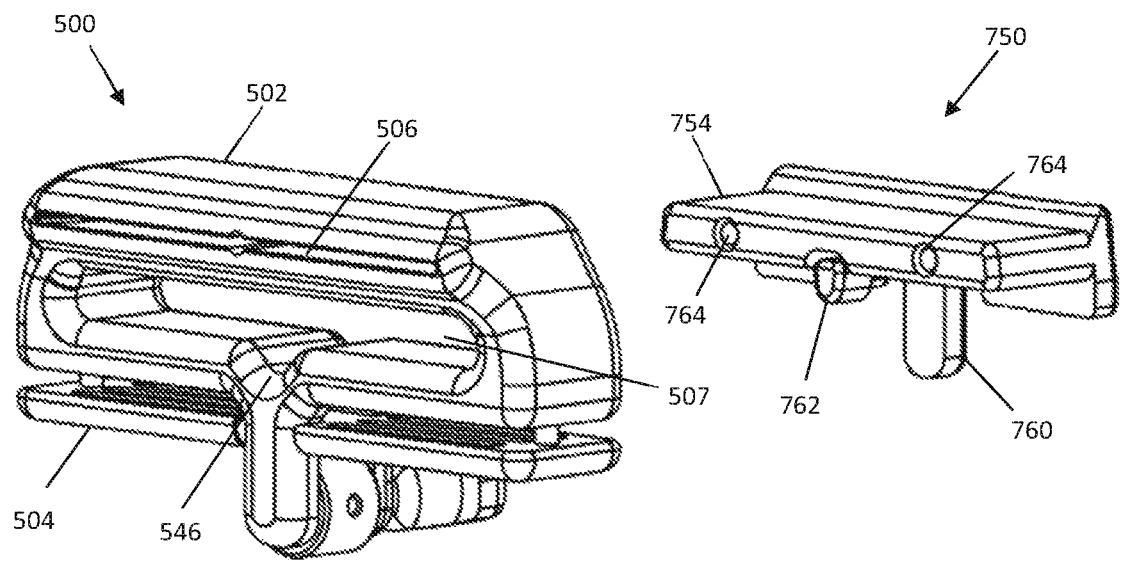
Figure 7E:
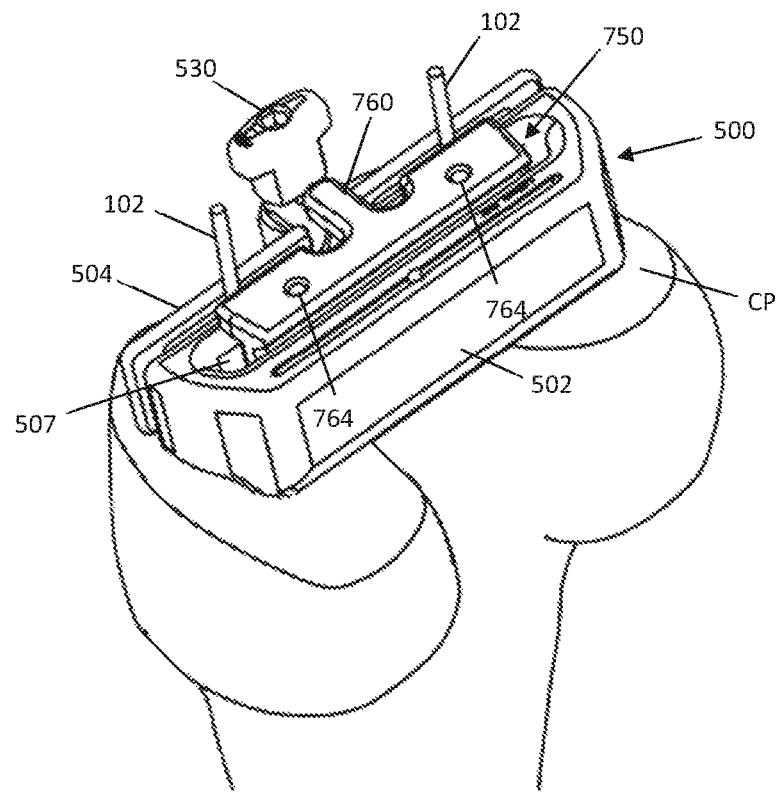

With reference to FIG. 7D, an exploded view of the saw guide 500 and insert drill guide 750 is shown. The insert drill guide 750 is inserted into the drill guide slot 507 of the saw guide 500. The drill guide slot 507 further includes a channel 546 notched into a side of the drill guide slot 507. The channel 546 receives the built-in spring 762 as the insert drill guide 750 is inserted into the drill guide slot 507. The built-in spring 762 imposes a force on the channel 546 due to the bending cantilever action of the spring 762. The built-in spring 762 therefore holds the insert drill guide 750 in the drill guide slot 507. FIG. 7E depicts the saw guide 500 and insert drill guide 750 assembled on bone pins 102 on the distal cut plane CP of the femur, where a user can then drill through the pair of holes 764 to create the holes for the pegs 612 of the N-in-1 block according to the planned POSE. The insert drill guide 750 is particularly advantageous because the drill guide 700 is no longer needed. The insert drill guide 750 is a single piece of material and does not require a clamp locking mechanism (408, 508, 708) to assemble to the bone pins 102 itself. This reduces the overall materials needed to perform a TKA, which reduces the overall costs. In addition, the insert drill guide 750 can be sterilized much easier than the drill guide 700 for use in subsequent procedures.

Overall, one of the main advantaged of the guides (400, 500, 700, 750) in general, is their universality because they may be used for any type of implant and any type of patient. In addition, the guides (400, 500, 700, 750) may be sterilized and re-used for multiple surgeries, greatly reducing the overall cost of TKA. The clamp locking mechanisms (408, 508, 708) allow the user to quickly and efficiently assemble/disassemble the guides (400, 500, 700, 750) to and from the bone pins 102 which reduces the overall time of the surgery and the amount of effort required by the user. Another primary advantage of the guides (400, 500, 700, 750) compared to conventional cutting guides used in orthopedic surgery is the clamping slot CS. Conventional guides do not have clamping slots, but rather utilize one or more securing pins/screws that screw the conventional guides directly to the bone. This is in contrast to the system and methods of the present application, where the bone pins 102 of the present application are inserted on the bone anywhere coincident with the virtual plane, allowing the clamping slot CS of the guides (400, 500, 700) to clamp to the bone pins 102 regardless of how far the bone pins are spaced on the bone (assuming the bone pins are not spaced farther than the total length of the clamping slot).

Surgical System and Procedure

Figure 8:
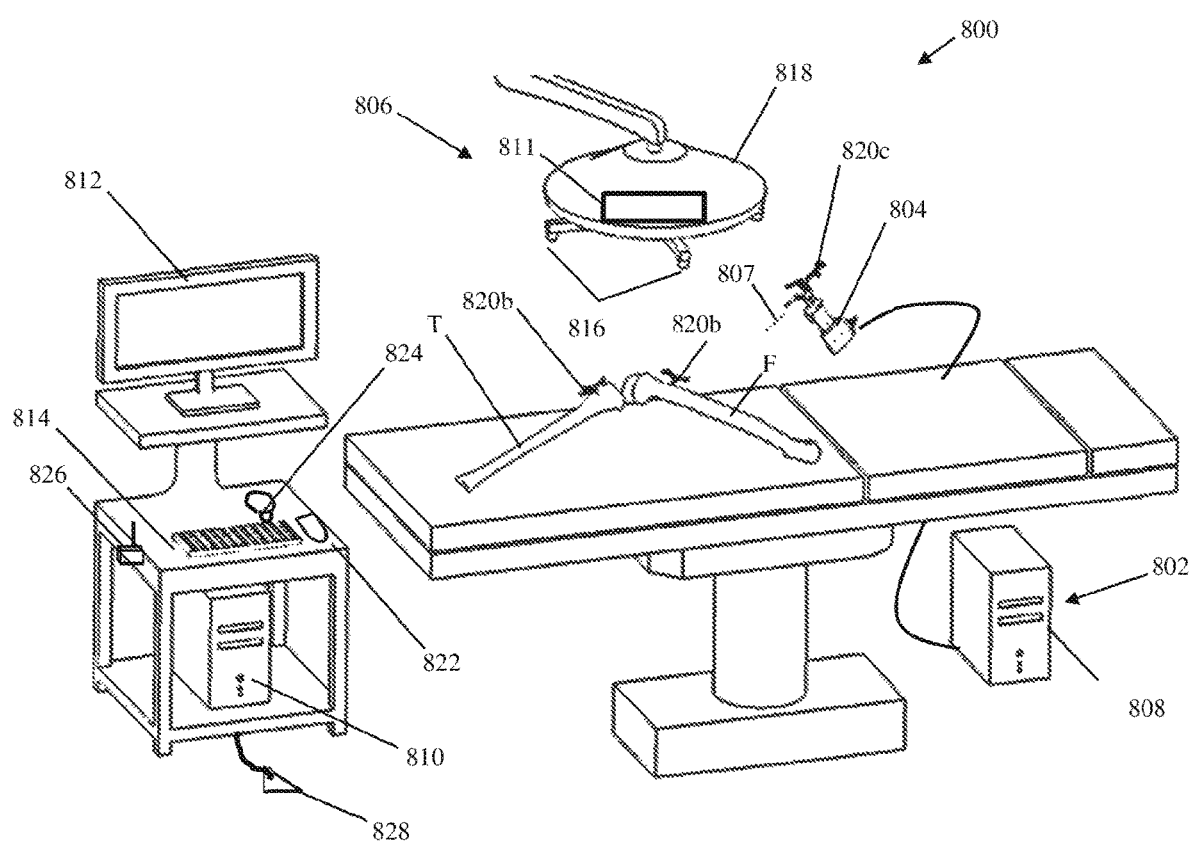
FIG. 8 depicts a prior art surgical system to perform a procedure on a bone using inventive embodiments of the guide.

Various surgical systems may be used to align and insert the bone pins 102 on virtual pin planes. In a particular inventive embodiment, as depicted in FIG. 8, a prior art 2-degree-of-freedom (2-DOF) surgical system 800 that utilizes a 2-DOF articulating surgical device 804 as described in U.S. Prov. Pat. App. No. 62/259,487 filed 24 Nov. 2015 and in PCT App. No. U.S. 2015/051713, assigned to the assignee of the present application and incorporated by reference herein in its entirety. The 2-DOF surgical system 800 generally includes a computing system 802, a surgical device 804, and a tracking system 806.

The computing system 802 generally includes hardware and software for executing a surgical procedure. The computing system 802 may include: a device computer 808 including a processor; a planning computer 810 including a processor; a tracking computer including a processor; one or more user interfaces, such as a display or monitor 812; and various user input mechanisms, illustratively including a keyboard 814, mouse 822, pendent 824, joystick 826, foot pedal 828, or a monitor 812 with touchscreen capabilities. In a particular inventive embodiment, the device computer 808 may include one or more processors, controllers, and any additional data storage medium such as RAM, ROM or other non-volatile memory to perform functions related to the operation of the surgical device 804. For example, the device computer 808 may include software, data, and utilities to control the surgical device 804, receive and process tracking data, execute registration algorithms, execute calibration routines, provide workflow instructions to the user throughout a surgical procedure, as well as any other suitable software, data or utilities required to successfully perform the procedure in accordance with embodiments of the invention. The planning computer 810 is preferably dedicated to planning the procedure either pre-operatively or intra-operatively. For example, the planning computer 810 may contain planning software, data, and utilities capable of receiving and reading medical imaging data, segmenting imaging data, constructing three-dimensional models, storing and providing computer-aided design (CAD) files, planning the POSE of the implants relative to the bone, generating surgical plan data for use with the system 800, and providing various functions to aid a user in planning the surgical procedure. The planning computer also contains software dedicated to defining virtual planes. The final surgical plan data may include an image data set of the bone, bone registration data, subject identification information, the POSE of the implant models relative to the bone modes, the POSE of one or more virtual planes defined relative to the bone, and any tissue modification instructions. The device computer 808 and the planning computer 810 may be directly connected in the operating room, or may exist as separate entities. The final surgical plan data is readily transferred to the device computer 808 and/or tracking computer 811 through a wired or wireless connection in the operating room (OR); or transferred via a non-transient data storage medium (e.g., a compact disc (CD), a portable universal serial bus drive (USB drive)) if the planning computer 810 is located outside the OR. The computing system 802 may act as a single entity, with multiple processors, capable of performing the functions of the device computer 808, the planning computer 810 and the tracking computer 811.

The computing system 802 accurately maintains the tool axis 807 in 3-D space based on the POSE of the virtual planes registered to the bone and the POSE data from the tracking system 806 as shown in FIG. 7. The tracking system 806 generally includes a detection device to determine the POSE of an object relative to the position of the detection device. In a particular embodiment, the tracking system 806 is an optical tracking system as described in U.S. Pat. No. 6,061,644, having two or more optical receivers 816 to detect the position of fiducial markers arranged on rigid bodies. Illustrative examples of the fiducial markers may include: an active transmitter, such as an LED or electromagnetic radiation emitter; a passive reflector, such as a plastic sphere with a retro-reflective film; or a distinct pattern or sequence of shapes, lines or other characters. A set of fiducial markers arranged on a rigid body is referred to herein as a fiducial marker array (820a, 820b, 820c), where each fiducial marker array (820a, 820b, 820c) has a unique geometry/arrangement of fiducial markers, or a unique transmitting wavelength/frequency if the markers are active LEDs, such that the tracking system 806 can distinguish between each of the tracked objects.

The tracking system 806 may be built into a surgical light 818, located on a boom, stand, or built into the walls or ceilings of the operating room. The tracking system computer 111 includes tracking hardware, software, data, and utilities to determine the POSE of objects (e.g. bones such as the femur F and tibia T, the surgical device 804) in a local or global coordinate frame. The POSE of the objects is referred to herein as POSE data, where this POSE data is readily communicated to the device computer 808 through a wired or wireless connection. Alternatively, the device computer 808 may determine the POSE data using the position of the fiducial markers detected directly from the optical receivers 816.

The POSE data is determined using the position of the fiducial markers detected from the optical receivers 116 and operations/processes such as image processing, image filtering, triangulation algorithms, geometric relationship processing, registration algorithms, calibration algorithms, and coordinate transformation processing.

POSE data from the tracking system 806 is used by the computing system 802 to perform various functions. For example, the POSE of a digitizer probe (not shown) with an attached probe fiducial marker array may be calibrated such that tip of the probe is continuously known as described in U.S. Pat. No. 7,043,961. The POSE of the tip or axis of the tool 807 may be known with respect to the device fiducial marker array 820c using a calibration method as described in Int'l Pat. App. No. WO 2016/141378. Registration algorithms are readily executed using the POSE data to determine the POSE and/or coordinate transforms between a bone, a surgical plan, and a surgical system. For example, in registration methods as described in U.S. Pat. Nos. 6,033,415 and 8,287,522, points on a patient's bone may be collected using a tracked digitizer probe to transform the coordinates of a surgical plan, coordinates of the bone, and the coordinates of a surgical device. The bone may also be registered using image registration as described in U.S. Pat. No. 5,951,475. The coordinate transformations may be continuously updated using the POSE data from a tracking system tracking the POSE of the bone post-registration and the surgical device.

It should be appreciated that in certain inventive embodiments, other tracking systems are incorporated with the surgical system 100 or replace the optical tracking system 806 such as an electromagnetic field tracking system, ultrasound tracking systems, accelerometers and gyroscopes, or a mechanical tracking system. The replacement of a non-mechanical tracking system with other tracking systems should be apparent to one skilled in the art. In specific embodiments, the use of a mechanical tracking system may be advantageous depending on the type of surgical system used such as the one described in U.S. Pat. No. 6,322,567 assigned to the assignee of the present application and incorporated by reference in its entirety.

In the surgical system 800, an optical tracking system 806 with optical receivers 816 is used to collect POSE data of the femur F and tibia T during total knee arthroplasty. The distal femur F and proximal tibia T are exposed as in a typical TKA procedure. Tracking arrays 820a and 820b are attached thereto and the femur F and tibia T are subsequently digitized and registered to a surgical plan. The POSE of the femur F and tibia T are tracked in real-time by the tracking system 806 so the coordinate transformation between the surgical plan and the surgical device are updated as the bones and surgical device move in the operating space. Therefore, a relationship between the POSE of the tool 807 and the POSE of any coordinates defined in the surgical plan may be determined by the computing system 802. In turn, the computing system 102 can supply actuation commands to the surgical device 804 in real-time to accurately maintain the tool axis of the tool 807 to the defined coordinates (e.g., virtual pin plane 316).

Additionally, user input mechanisms, illustratively including a trigger or foot pedal 828, may be used by the user to indicate to the computing system 802 that the tool axis 807 needs to be maintained to other coordinates defined in a surgical plan. For example, the tool axis 807 may be maintained in a first defined plane, and the user may step on the foot pedal 828 to relay to the computing system 802 that the tool axis 807 needs to be maintained in a second defined plane.

Figure 2:
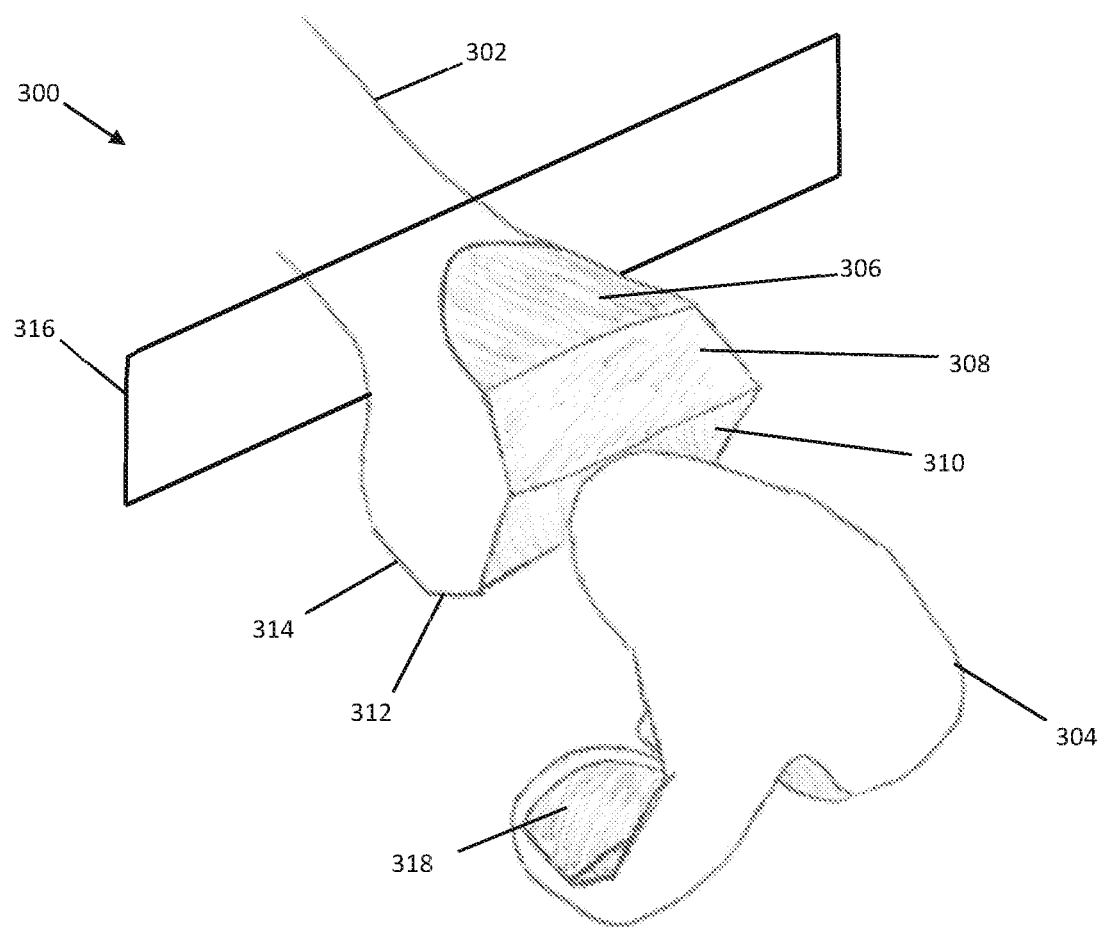
FIG. 2 illustrates a prior art view of a virtual pin plane defined relative to a planned cut plane on a three-dimensional (3-D) model of a bone.

The surgical plan is created, either pre-operatively or intra-operatively, by a user using planning software as described above. The final surgical plan contains the 3-D model of the patient's operative bone combined with the location of one or more virtual planes 316. The location of the virtual plane(s) 316 (as shown in FIG. 2) is defined by the planning software using the position and orientation (POSE) of one or more planned cut planes (306, 308, 310, 312, 314) and one or more dimensions of a guide (400, 500, 700). It is worth noting, that because the virtual planes are defined in the planning software based in part on certain dimensions of the guide (400, 500, 700) (e.g., the distance between the guide slot (406, 506) and the bottom surface (431, 531) of the guide portion (402, 502)), those portions of the guide (400, 500, 700) need to be manufactured with a tight tolerance so as to match the stored values of those dimensions in the planning software.

During the procedure, the user manipulates the surgical device 804 where the computing system 802 supplies actuation commands to actuators associated with the surgical device 804 to align the pin 102 with the pin plane 316. There are multiple advantages to using the 2-DOF articulating device 804 to accurately place the bone pins 102. For one, the surgical device 804 is actuating in real-time, therefore the user is actively guided to the POSE of the virtual pin plane. In addition, the correct position and orientation of the bone pins 102 is accurately maintained regardless of the surgeon's placement of the 2-DOF surgical system. Therefore, the user can place the pins in any arbitrary orientation (i.e. yaw) and position on the plane 316 and still attach the guide (400, 500, 700) to the pins 102 due to the unrestrictive clamping length of the clamping slot CS as described above. This greatly reduces the operational time of the procedure. In addition, the user can avoid any particular landmarks coincident with the virtual plane 316 if so desired.

A method of executing a TKA with the guide (400, 500) and the guide 700 is now described. A first virtual pin plane 316 is defined in the surgical plan by the planning software using the POSE of the planned distal cut plane 310, and the distance between the guide slot (406, 506) and the bottom surface (431, 531) of the guide portion (402, 502). The planning software may also use the known width of the bone pins 102. For example, the pin plane 316 can be defined by proximally translating the planned distal cut plane 310 by the distance between the guide slot (406, 506) and the bottom surface (431, 531) of the distal guide (400, 500). The software may further proximally translate the pin plane 316 by an additional half width of the pins 102. Therefore, when the guide (400, 500) is clamped to the bone pins 102, the guide slot (406, 506) will be aligned with the planned distal cut plane 310.

A second virtual pin plane (not shown) is defined for the guide 700. The second virtual plane is defined by: 1) defining a plane perpendicular to the planned distal cut plane 310 and parallel with the planned position for the cutting block pegs 612; 2) posteriorly translating that plane by the known distance between the centers of the guide holes (706, 764) and the clamping surface (431, 511, 715) of the guide portion (402, 502, 702); and 3) further posteriorly translating that plane by an additional half-width of the pins 102.

Intra-operatively, the user begins by inserting bone pins 102 on the first virtual pin plane. The user then clamps the guide (400, 500) to the bone pins 102 using the clamp locking mechanism (408, 508). The user then creates the distal cut plane CP by guiding a surgical saw through the guide slot (406, 506). The guide (400, 500) and bone pins 102 on the first virtual pin plane are then removed from the femur F. Next, the user inserts bone pins 102 on the second virtual pin plane directly on the distal cut plane CP surface. In one embodiment, the drill guide 700 is used to clamp to the bone pins 102 for creating the holes for the pegs 612 of the N-in-1 block 600. The drill guide 700 is clamped to the pins 102 using the clamp locking mechanism 708. The bone contacting surface 720 of the guide 700 lies flush with the distal cut plane CP surface. The user then drills the holes for the cutting block pegs 612 using the guide holes 706 as a guide. Subsequently, the pins 102 and the guide 700 are removed, the pegs 612 of an N-in-1 cutting block are placed in the drilled holes, and the remaining cut planes are created. In another embodiment, the saw guide (400, 500) and insert drill guide 750 is used to clamp to the bone pins 102 for creating the holes for the pegs 612 of the N-in-1 block 600. The saw guide (400, 500) is clamped to the pins 102 using the clamp locking mechanism (408, 508), where a face of the saw guide (400, 500) contacts the distal cut plane CP. The insert drill guide 750 is then inserted into the drill guide slot (446, 507). The user then drills the holes for the cutting block pegs 612 using the guide holes 764 as a guide. Subsequently, the saw guides (400, 500), insert drill guide 750, and bone pins 102 are removed, the pegs 612 of an N-in-1 cutting block are placed in the drilled holes, and the remaining cut planes are created.

OTHER EMBODIMENTS

While at least one exemplary embodiment has been presented in the foregoing detailed description, it should be appreciated that a vast number of variations exist. It should also be appreciated that the exemplary embodiment or exemplary embodiments are only examples, and are not intended to limit the scope, applicability, or configuration of the described embodiments in any way. Rather, the foregoing detailed description will provide those skilled in the art with a convenient roadmap for implementing the exemplary embodiment or exemplary embodiments. It should be understood that various changes can be made in the function and arrangements of elements without departing from the scope as set forth in the appended claims and the legal equivalents thereof.

The foregoing description is illustrative of particular embodiments of the invention, but is not meant to be a limitation upon the practice thereof. The following claims, including all equivalents thereof, are intended to define the scope of the invention.

The invention claimed is:

1. A saw guide for guiding a surgical saw to create one or more planar cuts on a bone, comprising:
    a guide portion having one or more guide slots, the one or more guide slot configured to guide a surgical saw to create the one or more bone cuts on the bone;
    an attachment portion assembled to the guide portion to form a clamping slot between the guide portion and the attachment portion; and
    a clamp locking mechanism having one or more cams assembled to the guide portion, the one or more cams in contact with the attachment portion to adjust the size of the clamping slot as the one or more cams are rotated to lock on to a set of bone pins inserted in the bone.

2. The saw guide of claim 1 wherein said guide portion is a stationary jaw body having the guide slot extending through the body, the stationary jaw body further comprising a bottom surface distanced from the guide slot and having a plurality of grooves for contracting the bone pins, a first coupling rod extending from a first side of the bottom surface and a second coupling rod extending from an opposing side of the bottom surface, wherein the first coupling rod and the second coupling rod are adapted to receive the attachment portion to form the clamping slot, and facilitate the assembly of said guide.

3. The saw guide of claim 2 wherein said first coupling rod further comprises a first opening, and said second coupling rod further comprises a second opening, wherein the first opening and the second opening are adapted to receive and pivotally hold a shaft associated with said clamp locking mechanism.

4. The saw guide of claim 1 wherein said guide portion further comprises two or more pin holes configured to receive two or more guide pins protruding from the attachment portion.

5. The saw guide of claim 1 wherein the attachment portion is a moveable jaw plate, the moveable jaw plate further comprising a top surface having a plurality of secondary grooves, a first notch for reception on a first coupling rod, a second notch for reception on a second coupling rod, and two or more pins that fit in a set of holes of said guide portion to prevent the clamping slot from overtightening on the bone pins.

6. The saw guide of claim 1 wherein the clamp locking mechanism further comprises a rotating knob, where rotation of the rotating knob adjusts the size of the clamping slot to secure and remove the guide from the bone pins.

7. The saw guide of claim 1 wherein the clamp locking mechanism further comprises an assembly shaft having a one or more keyseats that assembles the one or more cams, one or more washers, one or more keys, and the rotating knob.

8. The saw guide of claim 7 wherein the assembly shaft passes through an aperture of the coupling rod, and holds a first cam on a first side of the coupling rod and a second cam on an opposing second side of the coupling rod; and
    wherein with the first and second cam on opposing sides of the coupling rod, a uniform pressure is applied to the attachment portion as the user rotates the rotating knob.

9. The saw guide of claim 7 wherein the one or more keyseats and one or more keys increase rotational torque and prevent rotation between the assembly shaft and the one or more cams as the rotating knob is rotated.

10. The saw guide of claim 1 wherein the one or more cams further comprise eccentric cams, egg-shaped cams, ellipse cams, hexagon cams, dual cams, or a combination thereof.

11. The saw guide of claim 1 further comprising one or more springs positioned between the guide portion and the attachment portion, where the one or more springs are configured to keep the clamping slot expanded when the one or more cams are loosened.

12. The saw guide of claim 1 further comprising a mechanical stop, positioned between the attachment portion and the clamp locking mechanism, where the mechanical stop sets a maximum expansion distance of the clamping slot CS wherein the one or more cams are unloaded when fully loosened.

* * * * *